(12) United States Patent
Qiao et al.

(10) Patent No.: US 9,662,353 B2
(45) Date of Patent: May 30, 2017

(54) IRON-BASED MONTMORILLONITE MEDICAMENT FOR TREATING HYPERPHOSPHATEMIA AND IRON-DEFICIENCY ANEMIA, AND PREPARATION METHOD THEREFOR

(71) Applicants: Min Qiao, Jinan (CN); SHANDONG SIBANGDE PHARMACEUTICAL CO., LTD., Jinan (CN)

(72) Inventors: Min Qiao, Jinan (CN); Yijuan Yang, Jinan (CN); Gang Liu, Jinan (CN)

(73) Assignees: Min Qiao, Jinan (CN); SHANDONG SIBANGDE PHARMACEUTICAL CO., LTD., Jinan (CN)

( * ) Notice: Subject to any disclaimer, the term of this patent is extended or adjusted under 35 U.S.C. 154(b) by 0 days.

(21) Appl. No.: 14/786,718

(22) PCT Filed: Aug. 15, 2013

(86) PCT No.: PCT/CN2013/081557
§ 371 (c)(1),
(2) Date: Oct. 23, 2015

(87) PCT Pub. No.: WO2014/183347
PCT Pub. Date: Nov. 20, 2014

(65) Prior Publication Data
US 2016/0166609 A1    Jun. 16, 2016

(30) Foreign Application Priority Data
May 15, 2013    (CN) .......................... 2013 1 0180124

(51) Int. Cl.
*A61K 33/26* (2006.01)
*A61K 9/14* (2006.01)
*A61K 33/12* (2006.01)
*A61K 31/192* (2006.01)

(52) U.S. Cl.
CPC ................ *A61K 33/26* (2013.01); *A61K 9/14* (2013.01); *A61K 31/192* (2013.01); *A61K 33/12* (2013.01)

(58) Field of Classification Search
CPC .......... A61K 33/26; A61K 33/21; A61K 9/14; A61K 31/192
See application file for complete search history.

(56) References Cited

U.S. PATENT DOCUMENTS 5,536,852 A * 7/1996 Matsui .................... B01J 21/16
549/411

* cited by examiner

*Primary Examiner* — Ali Soroush
(74) *Attorney, Agent, or Firm* — CBM Patent Consulting, LLC

(57) ABSTRACT

It discloses an iron-based montmorillonite medicine for treating hyperphosphatemia and iron deficiency anaemia, and the preparation method thereof. The medicine comprises effective ingredient iron-based montmorillonite (Fe-montmorillonite) which is obtained by soaking or eluting the medicinal montmorillonite by water soluble iron salt solution. The effective ingredient is added by pharmaceutic adjuvant or not to make medicanent which is given via gastrointestinal tract. The effective ingredient binds the phosphate in the patients' digestive tract to form insoluble matter which can be excreted from the body via the digestive tract, therefore the phosphate in the patients with chronic renal failure is reduced and the goal of treating hyperphosphatemia is achieved.

5 Claims, 3 Drawing Sheets

Figure 1:
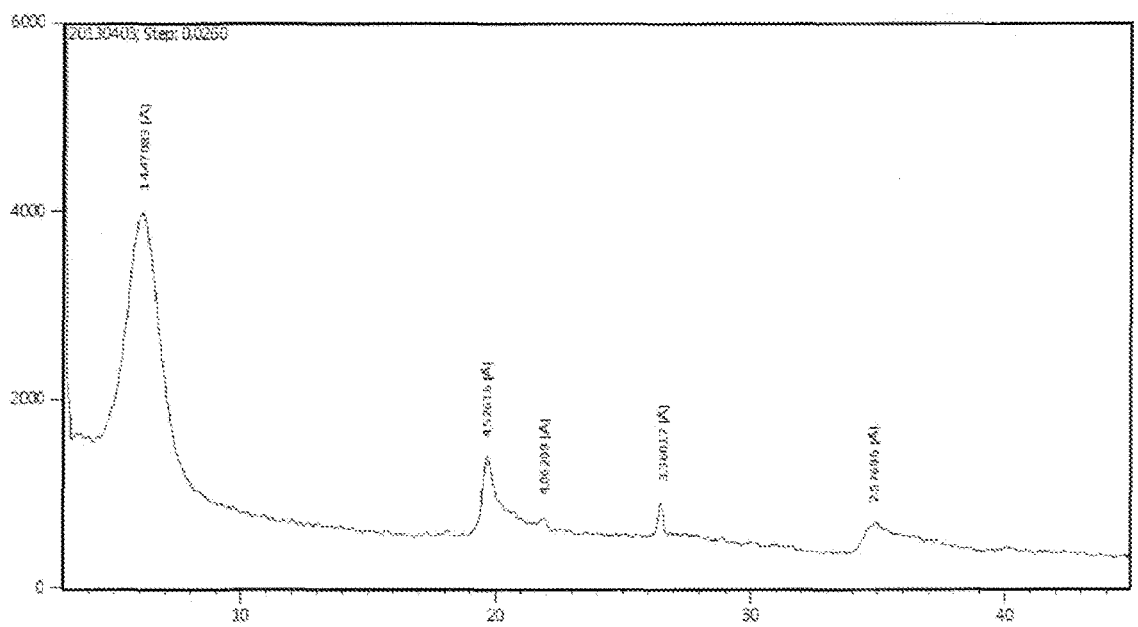

IRON-BASED MONTMORILLONITE MEDICAMENT FOR TREATING HYPERPHOSPHATEMIA AND IRON-DEFICIENCY ANEMIA, AND PREPARATION METHOD THEREFOR

This application is the U.S. national phase of International Application No. PCT/CN2013/081557 filed on 15 Aug. 2013 which designated the U.S. and claims priority to Chinese Application Nos. CN201310180124.8 filed on 15 May 2013, the entire contents of each of which are hereby incorporated by reference.

TECHNICAL FIELD

The present invention relates to an Iron-based montmorillonite medicine for treating hyperphosphatemia and iron deficiency anaemia and a preparation method therefore, belonging to the field of medicine technology.

BACKGROUND

Hyperphosphatemia is a common complication of chronic kidney disease (CKD), and it is an important factor to cause secondary hyperparathyroidism, the changes of calcium and phosphorus deposition, the metabolic disorders of vitamin D, and renal osteodystrophy. It is closely related with coronary calcification, valvular calcification and other serious cardiovascular complications. In the recent years, studies showed that a new type phosphate binding agent, lanthanum formulation, can effectively reduce the serum phosphorus level without causing secondary damage to the bone and hypercalcemia, and is a relatively safe phosphate binding agent, especially suitable for treating the patients with hyperphosphatemia who undergo a long-term hemodialysis. In general, as relatively safe therapeutic agents for treating hyperphosphatemia, aluminum hydroxide gel, calcium carbonate hydrate, calcium acetate hydrate, lanthanum carbonate hydrate and sevelamer can be used.

In the pathological presentation of hyperphosphatemia in chronic renal insufficiency, sometimes iron deficiency anemia or metabolic acidosis will happen. In this case, the anemia will further worsen if aluminum hydroxide gel is given. In addition, China patent literature CN100398112C (application NO. 200610043267.4) disclosed a medicine for treating hyperphosphatemia and a preparation method therefore, including an agent made from pharmaceutical effective ingredient, polystyrene sulfonic lanthanum, and pharmaceutic adjuvant. However, polystyrene sulfonic lanthanum can absorb iron when it undergoes ion exchange through the human digestive tract, therefore inhibit the iron absorption by intestinal, reduce the iron concentration and white blood cell hematocrit value in the blood and tissue of dialysis patients, finally aggravate the iron deficiency anemia of the dialysis patients. Similarly, WO94/27621 disclosed a method of binding iron ion by using an amino group-containing polymer; however, if the amino group-containing polystyrene and acrylic acid resins are given in the same way, the phenomena of the iron deficiency anemia will present. China patent literature CN1102393C (application NO. 96193918.4) disclosed a medical composition comprising a chosen lanthanum carbonate hydrate; in addition, China patent literature CN102573807A (application NO. 201080041895.3) disclosed a method of treating hyperphosphatemia by ferric citrate formulation. However, the two methods mentioned above will have side effect of irritation on the gastrointestinal tract in patients with renal failure.

THE CONTENT OF THE INVENTION

Aiming at the deficiency of existing technology, the present invention provided an Iron-based montmorillonite (Fe-montmorillonite) medicine for treating hyperphosphatemia and iron deficiency anaemia of the patients with chronic renal failure, and the present invention also provided a preparation method of the medicine.

SUMMARY OF THE INVENTION

The present invention takes iron-based montmorillonite (Fe-montmorillonite) as the pharmaceutical effective ingredient, add suitable pharmaceutic adjuvant or not to make medicanent, and gives the drug via gastrointestinal tract. The effective ingredient of the present invention binds the phosphate in the patients' digestive tract to form insoluble matter which can be excreted from the body via the digestive tract, therefore the phosphate in the patients with chronic renal failure is reduced and the goal of treating hyperphosphatemia is achieved.

Montmorillonite is a laminated mineral comprised of hydrous aluminum silicate with extremely fine particles. It is a clay mineral with three lamellar structure comprised of silicon oxygen tetrahedron, and contains some exchangeable cations among the interlayer of the crystal structure. The present invention is based on the cation exchange property of the montmorillonite. The interlayer can exchange the cations including mainly $Na^+$, $Ca^{2+}$, and secondly $K^+$, $Li^+$ and so on. The present invention treats the interlayer of montmorillonite to change its cation exchange property and changes montmorillonite into iron-based montmorillonite. The iron-based montmorillonite (Fe-montmorillonite) dissociates iron ion and montmorillonite in vivo, in which the iron ions bind the phosphate salts to form the insoluble material which is then excreted from the body, and the dissociated montmorillonite can not be absorbed by the human body, therefore the goal of treating hyperphosphatemia is achieved. Meanwhile, the iron ion, which is dissociated from iron-based montmorillonite (Fe-montmorillonite) and is unbound to the phosphate, is absorbed by the human body and supplies the iron ions in the body, therefore the goal of treating iron deficiency anaemia of the patients with chronic renal failure is achieved. The medicine of the present invention can also be used as preventive against hyperphosphatemia and iron deficiency anaemia of the patients with chronic renal failure.

DETAILED DESCRIPTION OF THE INVENTION

The technical scheme of the invention is as followed:

Iron-based montmorillonite medicine for treating hyperphosphatemia and iron deficiency anaemia, comprises pharmaceutical effective ingredient and/or pharmaceutic adjuvant. The pharmaceutical effective ingredient is iron-based montmorillonite (Fe-montmorillonite) which is 20~100% by weight in the medicine; the iron ion is 3.0~12.0% by weight in the iron-based montmorillonite (Fe-montmorillonite); the iron-based montmorillonite (Fe-montmorillonite) is obtained by soaking or eluting the medicinal montmorillonite by water soluble iron salt solution, in which the water soluble iron salt solution is ferrous gluconate, ferrous succinate, ferrous lactate, ferrous fumarate, or ferrous sulfat solution, and the medicinal montmorillonite is selected from calcium based montmorillonite (Ca-montmorillonite), sodium based montmorillonite (Na-montmorillonite) or magnesium based montmorillonite (Mg-montmorillonite). Medicinal montmorillonite is conventional raw material in the field which can be commercially purchased.

According to the present invention, preferred, the iron-based montmorillonite (Fe-montmorillonite) is 50~100% by weight in the medicine.

According to the present invention, preferred, the iron ion is 5.0~9.0% by weight in the iron-based montmorillonite (Fe-montmorillonite).

According to the present invention, preferred, the concentration of the water soluble iron salt solution is 5~15% by weight.

A preparation method of the iron-based montmorillonite medicine for treating hyperphosphatemia and iron deficiency anaemia, wherein the step comprises:

(1) adding pharmaceutical montmorillonite into deionized water, acidizing by treating with hydrochloric acid, adjusting the pH value to 2.0~3.5, treating by ultrasonication under stirring for 10~30 minutes; static standing, layering and separating the upper water, adding deionized water with the equal volume of the separated water for washing, separating the upper water again, repeating washing for several times until the pH value of the washing buffer reaches 6.5~7.5, filtering by plate and frame pressing, collecting the solid material, drying until the water content is no more than 10 wt %; then powdering by pulverizer until the particle diameter is no more than 45 μm, then screening under 325 mesh, checking chloride, comparing with control solution prepared by 5.0 ml standard sodium chloride solution, making the concentration of chloride no more than 0.025%;

(2) soaking or eluting the medicinal montmorillonite treated by step (1) by water soluble iron salt solution, washing by deionized water until the pH value reaches 6.5~7.5, washing out the excess non-exchanged iron ion, filtering, vacuum drying the solid material until the water content is no more than 10 wt %, powdering by pulverizer until the particle diameter is no more than 45 μm, then screening under 325 mesh, obtaining the iron-based montmorillonite (Fe-montmorillonite), checking the ion content of the iron-based montmorillonite. The iron ion content of the obtained iron-based montmorillonite (Fe-montmorillonite) is 3.0~12.0% by weight;

(3) Taking the iron-based montmorillonite (Fe-montmorillonite) obtained by step (2) as pharmaceutical effective ingredient to prepare powder, capsule, tablet, dry suspension, suspension or granules.

According to the present invention, preferred, the ultrasonic frequency in the ultrasonic treatment of the step (1) is 30~40 KHz.

According to the present invention, preferred, in the step (2), soaking or eluting by water soluble iron salt solution under the temperature of 0~40, soaking for 5~72 hours or eluting for 5~72 hours. More preferred, soaking or eluting by water soluble iron salt solution under the temperature of 20~30, soaking for 24~48 hours or eluting for 24~48 hours. The soaking or eluting time is related to the concentration of the water soluble iron salt solution and can be adjusted according to the concentration of the soluble salt.

According to the present invention, preferred, in the step (3), powdering the iron-based montmorillonite (Fe-montmorillonite) until the particle diameter is no more than 45 μm, then screening under 325 mesh and directly making into powder without pharmaceutic adjuvant.

Alternatively, powdering the iron-based montmorillonite (Fe-montmorillonite) until the particle diameter is no more than 45 μm, then screening under 325 mesh and taking as pharmaceutical effective ingredient, adding pharmaceutic adjuvant to prepare powder, capsule, tablet, dry suspension, suspension or granules. The pharmaceutic adjuvant is any sort that used in the field of medicine, and the addition amount of the pharmaceutic adjuvant is according to the conventional technology.

According to the present invention, preferred, in the step (3), the iron ion content is 5.0%, 6.0%, 6.5%, 7.0%, 7.5%, 8.0% or 9.0% by weight in the iron-based montmorillonite.

The water used in the present invention is deionized water.

In the present invention, the iron content is 3.0~9.0% by weight in the iron-based montmorillonite (Fe-montmorillonite) and can also be less than 3.0%. Since more oral drug dosage is needed when the iron ion content is less than 3.0% by weight, the present invention further optimizes the iron ion content in the iron-based montmorillonite (Fe-montmorillonite) to be 5.0~9.0% by weight.

The experiments of the present invention demonstrate that the iron-based montmorillonite (Fe-montmorillonite) can be given via gastrointestinal tract to treat hyperphosphatemia, iron deficiency anaemia and dialysis-induced iron deficiency anaemia.

For treating hyperphosphatemia and iron deficiency anaemia, the daily oral dosage of the iron-based montmorillonite (Fe-montmorillonite) medicine for adult in the present invention is according to the weight of the iron-based montmorillonite (Fe-montmorillonite) which is appropriate 4.0~9.0 g. The patient with special constitution should depend on the situation and follow the doctor's advice.

The beneficial effects of the present invention are as follows:

1. The iron-based montmorillonite (Fe-montmorillonite) medicine for treating hyperphosphatemia and iron deficiency anaemia in the present invention has good dephosphorylated effect in the human stomach, small intestine, large intestine and the digestive tract. The iron-based montmorillonite (Fe-montmorillonite) wan dissociated to be free iron ions and montmorillonite in vivo, in which the iron ions bind the phosphate salts to form the insoluble material which is then excreted from the body, and the rest of the iron ions are absorbed by the human body, therefore play the role of treating iron deficiency anemia.

2. The preparation cost of the iron-based montmorillonite (Fe-montmorillonite), appropriate adjuvant and the iron-based montmorillonite medicine for treating hyperphosphatemia and iron deficiency anaemia in the present invention are low, which can reduce the economic burden of patients and achieve good social benefits.

3. After administrated of the iron-based montmorillonite medicine for treating hyperphosphatemia and iron deficiency anaemia in the present invention by oral and via the gastrointestinal tract, the symptoms of hyperphosphatemia and iron deficiency anaemia can be treated.

FIGURE DESCRIPTION

FIG. 1 the X-ray diffraction spectrum of the montmorillonite standard. The abscissa is 2θ (°), the ordinate is intensity (arbitrary unit).

Figure 2:
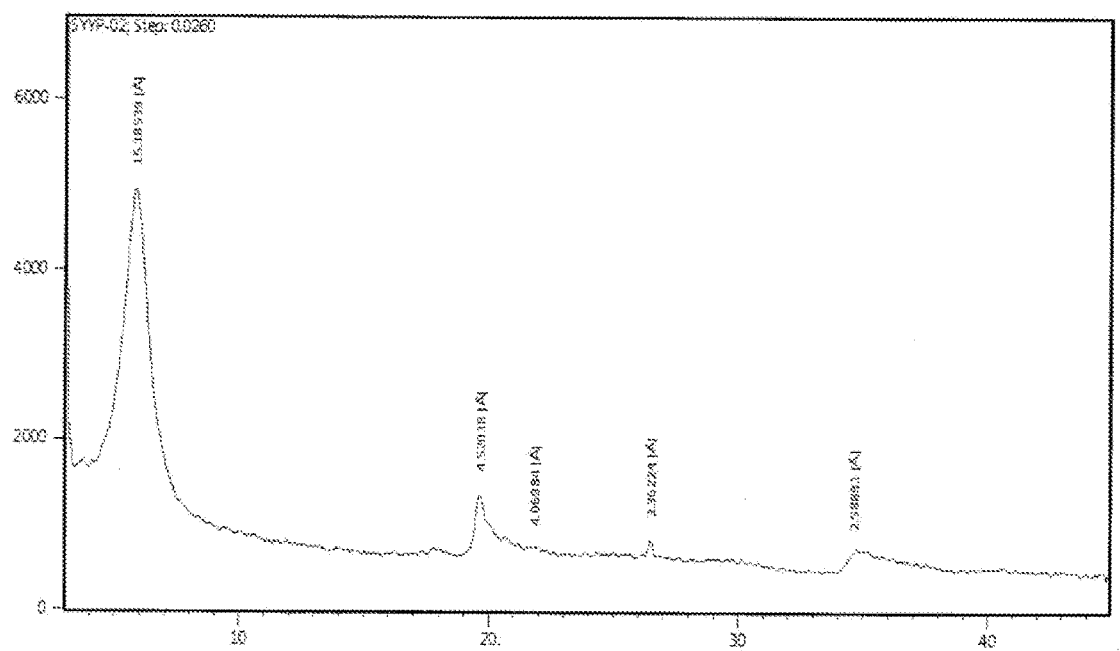

FIG. 2 the X-ray diffraction spectrum of the treated montmorillonite in the step (1) of example 1. The abscissa is 2θ (°), the ordinate is intensity (arbitrary unit).

Figure 3:
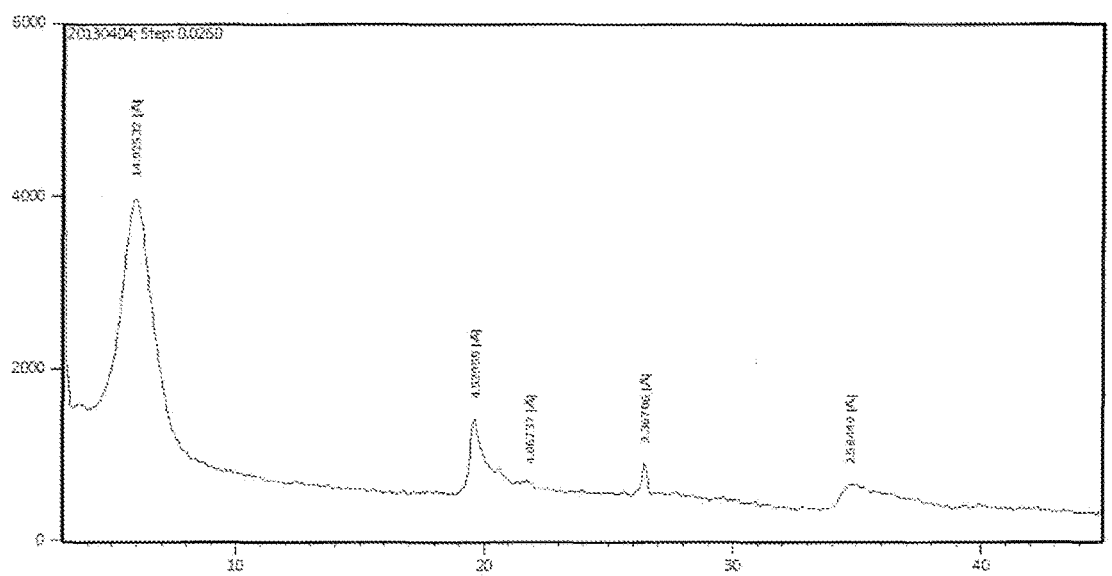

FIG. 3 the X-ray diffraction spectrum of the iron-based montmorillonite obtained in the step (2) of example 1. The abscissa is 2θ (°), the ordinate is intensity (arbitrary unit).

EMBODIMENT

The following embodiments combined with the attached figures are given to further illustrate the present invention rather than to limit its scope.

In the present invention, the concentration of the water soluble iron salt solution is by weight. The montmorillonite used in examples 1~8 is calcium-based montmorillonite (Ca-montmorillonite).

The illustration of the raw adjuvant in the examples:

| Name of the raw adjuvant | Manufactory company | Executive standard |
|---|---|---|
| montmorillonite | Shandong Xianhe pharmaceutical limited company | WS1-(X-165)-2004Z |
| ferrous sulfate | Anji Haosen pharmaceutical limited company | Chinese Pharmacopoeia 2010 edition, second section |
| ferrous succinate | Chengdu Li'er pharmaceutical limited company | Chinese raw drug quality standard assembly |
| ferrous gluconate | Guangzhou Yuandong pharmaceutical limited company | Chinese Pharmacopoeia 2010 edition, second section |
| ferrous fumarate | Shanghai Xudonghaipu pharmaceutical limited company | Chinese Pharmacopoeia 2010 edition, second section |
| ferrous lactate | Tonghua Jitong pharmaceutical limited company | Chinese raw drug quality standard assembly |
| deionized water | Shandong Sibangde pharmaceutical limited company | Chinese Pharmacopoeia 2010 edition, second section |
| hydrochloric acid | Hunan Erkang pharmaceutical limited company | Chinese Pharmacopoeia 2010 edition, second section |

EXAMPLE 1

A preparation method of the iron-based montmorillonite medicine for treating hyperphosphatemia and iron deficiency anaemia, wherein the step comprises:

(1) Weighing 200 g montmorillonite, putting them into the ultrasonic generator equipped with mixing function, then adding 2000 g deionized water that has been measured, stirring with the speed of 30 r/min, acidizing by treating with 5N hydrochloric acid until the pH value reaches to 2.0, treating by ultrasonication with 30 KHz for 30 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 5.6% by weight, powdering and screening under 325 mesh;

Taking the X-ray powder diffraction experiment of the montmorillonite sample obtained above, weighing 4 g montmorillonite obtained above and grinding them to be fine powder, taking appropriate amount of the fine powder, putting them on the loading frame which is then put into the dryer (containing saturated sodium chloride solution, with the relative humidity of about 75% in 20), getting it out after about 12 hours, flattening the sample on the loading frame, measuring according to the X-ray powder diffraction method (Chinese Pharmacopoeia 2010 edition, second section, appendix IX F), scanning in the scope of diffraction angle (2θ) from 2° to 80°. FIG. 2 illustrates the X-ray diffraction spectrum of montmorillonite prepared in the present example. It is consistent with the characteristic peaks in the X-ray diffraction spectrum of the standard montmorillonite (FIG. 1) (the diffraction angles (2θ) are 5.8°, 19.8° and 61.9°, respectively), indicating that the chemical structure of montmorillonite is not disrupted when the pH value is adjusted to 2.0 by 5N medicinal hydrochloric acid.

(2) Weighing 100 g montmorillonite prepared by step (1), putting them into the reactor equipped with mixing function, then adding 500 g deionized water that has been measured, stirring with the speed of 30 r/min, adding 800 ml 15 wt % ferrous sulfate after stirring for 40 min, continue stirring for 12 hours at the temperature of 30, static standing for 24 hours, separating the upper water, adding deionized water with the equal volume of the separated water for repeated washing until the pH value reaches to 6.5, continue washing until the excess iron ion is cleaned up, filtering by pressing, drying to obtain iron-based montmorillonite (Fe-montmorillonite), making the water content be 5.6% by weight, powdering and screening under 325 mesh, obtaining lactate iron-based montmorillonite (Fe-montmorillonite). The iron ion content is 7.8% by weight in the iron-based montmorillonite (Fe-montmorillonite) by measurement.

(3) Taking the iron-based montmorillonite (Fe-montmorillonite) prepared by step (2) as powder, taking directly.

Taking the X-ray powder diffraction experiment of the iron-based montmorillonite sample obtained above, FIG. 3 illustrates the X-ray diffraction spectrum of the iron-based montmorillonite prepared in the present example. It is consistent with the characteristic peaks in the X-ray diffraction spectrum of the standard montmorillonite (the diffraction angles (2θ) are 5.8°, 19.8° and 61.9°, respectively).

Effect Experiment 1

To further testify that the iron-based montmorillonite medicine for treating hyperphosphatemia and iron deficiency anaemia in the present invention has good dephosphorylated effect in the human digestive tract, the base liquids of artificial gastric fluid, small intestine fluid, and large intestine fluid are prepared, respectively, and experiments are taken as follows:

① test solution 1: dissolving 8 g NaCl in 1000 ml distilled water, adjusting the pH value to 3 by using hydrochloric acid;
② test solution 2: dissolving 8 g NaCl in 1000 ml distilled water, adjusting the pH value to 6.8 by using hydrochloric acid;
③ test solution 3: dissolving 8 g NaCl in 1000 ml distilled water, adjusting the pH value to 7.8 by using hydrochloric acid;
④ test solution 4: dissolving 15 g anhydrous $Na_2HPO_4$ in 1000 ml distilled water, filtering, preparing to be base solution, measuring the content of phosphate.

Adding quantitative iron-based montmorillonite (Fe-montmorillonite) prepared by example 1 and test solution 4 into test solution 1, 2, and 3, respectively, making the molar ratio of iron ion and phosphate to be 3:1, fully stirring under 3° C., taking a certain amount of test solution, filtering, measuring the content of the phosphate, calculating the percentage of the removed phosphate in the test solution. The experiment results are shown in table 1.

TABLE 1 statistical table of the removed phosphate in the test solution

| | the removed phosphate (%) | | |
|---|---|---|---|
| | test solution 1 | test solution 2 | test solution 3 |
| 3 min | 64.5 | 68.2 | 67.2 |
| 5 min | 73.3 | 78.1 | 77.3 |
| 7 min | 84.8 | 89.1 | 88.8 |
| 9 min | 92.6 | 97.5 | 95.9 |

Conclusion can be obtained by analysis of the experiment result of Table 1: the iron-based montmorillonite (Fe-montmorillonite) has good dephosphorylated effect in artificial gastric fluid, small intestine fluid, and large intestine fluid, further indicating that the iron-based montmorillonite has good dephosphorylated effect in the human stomach, small intestine, large intestine and the digestive tract, thus confirming that the iron-based montmorillonite has good clinical significances in treating hyperphosphatemia.

EXAMPLE 2

A preparation method of the iron-based montmorillonite medicine for treating hyperphosphatemia and iron deficiency anaemia, wherein the step comprises:
(1) Weighing 300 g montmorillonite, putting them into the ultrasonic generator equipped with mixing function, then adding 3000 g deionized water that has been measured, stirring with the speed of 30 r/min, acidizing by treating with 5N hydrochloric acid until the pH value reaches to 2.6, treating by ultrasonication with 40 KHz for 20 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 9.1% by weight, powdering and screening under 400 mesh.
(2) Weighing 200 g montmorillonite prepared by step (1), putting them into the reactor equipped with mixing function, then adding 1500 g deionized water that has been measured, stirring with the speed of 30 r/min, after stirring for 4 hours, loading the column by wet method (column diameter:column height=1:6), keeping the column temperature at 30, eluting by 1500 ml 15 wt % ferrous sulfate, eluting for once, twice or three time, eluting for 36 hours, then washing with deionized water until the pH value reaches to 7.0, continue washing until the excess iron ion is cleaned up, vacuum drying the iron-based montmorillonite (Fe-montmorillonite) until the water content reaches 8.0% by weight, powdering and screening under 325 mesh, obtaining lactate iron-based montmorillonite (Fe-montmorillonite). The iron ion content is 8.7% by weight in the iron-based montmorillonite (Fe-montmorillonite) by measurement.
(3) Preparing the iron-based montmorillonite (Fe-montmorillonite) prepared by step (2) as particles, loading them into conventional capsule or enteric capsule to obtain medicinal capsule by adding conventional amount of pharmaceutic adjuvant and appropriate wetting agent. The detailed method is according to the current conventional technology in the field.

Effect Experiment 2

The experiment about the therapeutical effect of the iron-based montmorillonite (Fe-montmorillonite) on chronic renal failure (CRF) caused hyperphosphatemia.
(1) Medicine: the iron-based montmorillonite prepared by example 2, grinding into fine powder in a mortar for use.
(2) Animal: the class of Golden hamster is ordinary level, provided by the Animal Center of Shandong University, with the weight of 120 g±20 g.

The experiment is as follows:
Taking 30 Golden hamster with the weight of 120 g±20 g, grouping by random:
① 10 for normal control group, intragastric administrating daily with water by 2 ml/120 g after keeping feeding for 2 weeks;
② 10 for model control group, intragastric administrating daily with 0.5% adenine by 2 ml/120 g;
③ 10 for treatment group, intragastric administrating daily with 0.5% adenine by 2 ml/120 g, and after 2 weeks, intragastric administrating daily with iron-based montmorillonite (Fe-montmorillonite) by 300 mg/kg.

Keeping intragastric administrating above animals for 6 weeks, taking blood from the rats from the sixth week, and detecting the blood phosphorus content, respectively. The results are shown in Table 2.

TABLE 2 the experiment results of chronic renal failure caused hyperphosphatemia

| | number | 6 weeks P(mol/L) |
|---|---|---|
| normal control group | 10 | 2.82 ± 0.26 |
| model control group | 10 | 5.42 ± 0.33 |
| treatment group | 10 | 3.32 ± 0.24 |

The comparison of model control group to normal control group for 6 weeks (P<0.05); the comparison of model control group to normal control group for 6 weeks (P<0.05).

Conclusion: the iron-based montmorillonite (Fe-montmorillonite) can reduce the blood phosphorus content of the rats with hyperphosphatemia.

Effect Experiment 3

The experiment about the therapeutical effect of the iron-based montmorillonite (Fe-montmorillonite) on chronic renal failure caused anemia.
(1) Medicine: the iron-based montmorillonite prepared by example 2, grinding into fine powder in a mortar for use.
(2) Animal: the class of Golden hamster is ordinary level, provided by the Animal Center of Shandong University, with the weight of 120 g±20 g.
The experiment is as follows:
taking 30 healthy male Golden hamster with the weight of 120 g±20 g, grouping by random:
① 10 for normal control group, intragastric administrating daily with water by 2 ml/120 g after keeping feeding for 2 weeks;
② 10 for model control group, intragastric administrating daily with 0.5% adenine by 2 ml/120 g;
③ 10 for treatment group, intragastric administrating daily with 0.5% adenine by 2 ml/120 g, and after 2 weeks, intragastric administrating daily with iron-based montmorillonite (Fe-montmorillonite) by 300 mg/kg.
Keeping intragastric administrating above animals for 6 weeks, taking blood from the rats from the sixth week, and detecting RBC, HB, HCT, EPO, SP, ALB of the animals, respectively. The results are shown in Table 3 and 4.

TABLE 3 the experiment results of RBC, HB and HCT
of chronic renal failure caused anemia

|  | number | RBC($10^{10}$) | HB(g/l) | HCT(%) |
| --- | --- | --- | --- | --- |
| normal control group | 10 | 6.70 ± 0.54 | 125.5 ± 7.4 | 40.7 ± 3.20 |
| model control group | 6 | 5.20 ± 0.25 | 90.0 ± 5.7 | 34.5 ± 1.75 |
| treatment group | 8 | 6.50 ± 0.52 | 117.0 ± 7.7 | 39.7 ± 3.30 |

TABLE 4 the experiment results of EPO, SP and ALB
of chronic renal failure caused anemia

|  | number | PO(mu/ml) | SP(g/l) | ALB(g/l) |
| --- | --- | --- | --- | --- |
| normal control group | 10 | 9.15 ± 0.67 | 78.85 ± 1.61 | 41.85 ± 2.30 |
| model control group | 6 | 5.70 ± 1.91 | 65.75 ± 3.78 | 31.05 ± 1.73 |
| treatment group | 8 | 7.53 ± 0.57 | 73.50 ± 1.78 | 36.30 ± 1.67 |

Conclusion: the iron-based montmorillonite (Fe-montmorillonite) can to some extent improve the reduction of RBC, HB and HCT of rat chronic renal failure caused anemia model established by adenine. The difference was statistically significant. The iron-based montmorillonite (Fe-montmorillonite) also can to some extent improve the reduction of EPO, SP and ALB.

EXAMPLE 3

A preparation method of the iron-based montmorillonite medicine for treating hyperphosphatemia and iron deficiency anaemia, wherein the step comprises:

(1) Weighing 400 g montmorillonite, putting them into the ultrasonic generator equipped with mixing function, then adding 4000 g deionized water that has been measured, stirring with the speed of 30 r/min, acidizing by treating with 5N hydrochloric acid until the pH value reaches to 3.0, treating by ultrasonication with 40 KHz for 10 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 7.6% by weight, powdering and screening under 400 mesh.

(2) Weighing 200 g montmorillonite prepared by step (1), putting them into the reactor equipped with mixing function, then adding 1000 g deionized water that has been measured, stirring with the speed of 30 r/min, after stirring for 4 hours, loading the column by wet method (column diameter:column height=1:6), keeping the column temperature at 30, eluting by 5000 ml 10 wt % ferrous succinate, eluting for 36 hours, then washing with deionized water until the pH value reaches to 6.8, continue washing until the excess iron ion is cleaned up, vacuum drying the iron-based montmorillonite (Fe-montmorillonite) until the water content reaches 5.0% by weight, powdering and screening under 325 mesh, obtaining lactate iron-based montmorillonite (Fe-montmorillonite). The iron ion content is 7.4% by weight in the iron-based montmorillonite (Fe-montmorillonite) by measurement.

(3) Preparing the iron-based montmorillonite (Fe-montmorillonite) prepared by step (2) as particles by adding conventional amount of pharmaceutic adjuvant and appropriate wetting agent, then obtaining tablet by compression. The detailed method is according to the current conventional technology in the field.

Experiment 3

The experiment about the effect of soaking or eluting temperature and time on the iron ion content in the iron-based montmorillonite (Fe-montmorillonite)

In the preparation method of the iron-based montmorillonite medicine for treating hyperphosphatemia and iron deficiency anaemia in the present invention, the iron ion content in the iron-based montmorillonite (Fe-montmorillonite) is related to the reaction temperature and time of montmorillonite and water soluble iron salt solution on condition that the water soluble iron salt solution is quantified. When the time is longer, the iron ion content in the prepared iron-based montmorillonite (Fe-montmorillonite) is more, and the yield is higher; in the contrast, the iron ion content is less, and the yield is lower. When the temperature is higher, the iron ion content in the prepared iron-based montmorillonite (Fe-montmorillonite) is relatively more, and the yield is higher; in the contrast, the yield is lower. The experiment data are shown in table 5 and 6.

1, 2, 3 and 4 in Table 5 show the obtained iron-based montmorillonite (Fe-montmorillonite) under different conditions when the ratio of montmorillonite, and ferrous succinate is 1:6 by weight. Preparation is carried out under different times according to the method in the present invention. The experiment results are shown in Table 5.

TABLE 5 comparison of prepared iron-based montmorillonite
(Fe-montmorillonite) under different times

| | Temperature (° C.) | Time (h) | the iron ion content in the iron-based montmorillonite (Fe-montmorillonite) by weight (%) |
|---|---|---|---|
| 1 | 30 | 60 | 10.2 |
| 2 | 30 | 48 | 9.2 |
| 3 | 30 | 36 | 7.6 |
| 4 | 30 | 24 | 6.8 |

1, 2, 3 and 4 in Table 6 show the obtained iron-based montmorillonite (Fe-montmorillonite) under different conditions when the ratio of montmorillonite, and ferrous succinate is 1:6 by weight. Preparation is carried out under different temperatures according to the method in the present invention. The experiment results are shown in Table 6.

TABLE 6 comparison of prepared iron-based montmorillonite
(Fe-montmorillonite) under different temperatures

| | temperature (° C.) | time (h) | the iron ion content in the iron-based montmorillonite (Fe-montmorillonite) by weight (%) |
|---|---|---|---|
| 1 | 50 | 48 | 11.1 |
| 2 | 40 | 48 | 10.3 |
| 3 | 30 | 48 | 9.2 |
| 4 | 20 | 48 | 7.2 |

The preparation temperature in the above Table 5 and Table 6 can be 0~50. Because the reaction time needs to be relatively longer when the temperature is lower, which is unfavourable for industrialized production, it is preferred to adopt 30~40.

EXAMPLE 4

A preparation method of the iron-based montmorillonite medicine for treating hyperphosphatemia and iron deficiency anaemia, wherein the step comprises:

(1) Weighing 500 g montmorillonite, putting them into the ultrasonic generator equipped with mixing function, then adding 5000 g deionized water that has been measured, stirring with the speed of 30 r/min, acidizing by treating with 5N hydrochloric acid until the pH value reaches to 3.5, treating by ultrasonication with 40 KHz for 25 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 8.8% by weight, powdering and screening under 400 mesh.

(2) Weighing 200 g montmorillonite prepared by step (1), putting them into the reactor equipped with mixing function, then adding 1000 g deionized water that has been measured, stirring with the speed of 30 r/min, after stirring for 4 hours, loading the column by wet method (column diameter:column height=1:6), keeping the column temperature at 20, eluting by 6000 ml 8.0 wt % ferrous fumarate, eluting for 24 hours, then washing with deionized water until the pH value reaches to 7.0, continue washing until the excess iron ion is cleaned up, vacuum drying the iron-based montmorillonite (Fe-montmorillonite) until the water content reaches 6.5% by weight, powdering and screening under 325 mesh, obtaining lactate iron-based montmorillonite (Fe-montmorillonite). The iron ion content is 7.1% by weight in the iron-based montmorillonite (Fe-montmorillonite) by measurement.

(3) Preparing the iron-based montmorillonite (Fe-montmorillonite) prepared by step (2) as dry suspension by adding and mixing evenly with conventional amount of pharmaceutic adjuvant. The detailed method is according to the current conventional technology in the field.

EXAMPLE 5

A preparation method of the iron-based montmorillonite medicine for treating hyperphosphatemia and iron deficiency anaemia, wherein the step comprises:

(1) Weighing 300 g montmorillonite, putting them into the ultrasonic generator equipped with mixing function, then adding 3000 g deionized water that has been measured, stirring with the speed of 30 r/min, acidizing by treating with 5N hydrochloric acid until the pH value reaches to 2.8, treating by ultrasonication with 35 KHz for 15 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 9.0% by weight, powdering and screening under 400 mesh.

(2) Weighing 150 g montmorillonite prepared by step (1), putting them into the reactor equipped with mixing function, then adding 750 g deionized water that has been measured, stirring with the speed of 30 r/min, after stirring for 40 minutes, adding 4500 ml 5 wt % ferrous gluconate, keeping the temperature at 35, continue stirring for 4 hours, then static standing for 36 hours, separating the upper water, adding deionized water with the equal volume of the separated water for repeated washing until the pH value reaches to 7.2, continue washing until the excess iron ion is cleaned up, filtering by pressing, vacuum drying until the water content reaches 7.9% by weight, obtaining iron-based montmorillonite (Fe-montmorillonite), vacuum drying until the water content reaches 7.8% by weight, powdering and screening under 325 mesh, obtaining lactate iron-based montmorillonite (Fe-montmorillonite). The iron ion content is 8.2% by weight in the iron-based montmorillonite (Fe-montmorillonite) by measurement.

(3) Preparing the iron-based montmorillonite (Fe-montmorillonite) prepared by step (2) as suspension by adding and mixing evenly with conventional amount of pharmaceutic adjuvant and water. The detailed method is according to the current conventional technology in the field.

Effect Experiment 5

The experiment about the absorption effect of the iron-based montmorillonite (Fe-montmorillonite) onto bile acid Medicine: iron-based montmorillonite, iron-based montmorillonite prepared by example 5, grinding into fine powder in a mortar for use.

Cholestyramine, purchased from Nanjing Housheng pharmaceutical limited company.

Bile acid, purchased from Shanghai Hengyuan biotechnology limited company.

Bile acid standard sample (Sigma company).

The experiment is as follows:

Adding 2 ml 5 mmol/L bile acid solution into 2 ml 2 mg/ml iron-based montmorillonite sample suspension and 2 ml 2 mg/ml cholestyramine sample suspension, respectively, after stirring for 0.5 hours at 37, filtering by 0.45 μm millipore filter, measuring the bile acid content in the filtrate.

Detecting instrument: 1100 type high performance liquid chromatography-mass spectrometry (Agilent company), equipped with four gradient pump, 100 units automatic sampler, fluorescence detector, online vacuum degas machine, and atmospheric pressure chemical ionization source (APCI); HypersilC18 chromatography column (4.6 mm×200 mm, 5 μm, Dalian institute of chemical physics, Chinese academy of sciences).

Detecting agents: 1,2-benz-3,4-dihydrocarbazole-9-ethyl p-toluenesultonate;

Acetonitrile-anhydrous (Yucheng chemical reagent factory), distilling after drying by $P_2O_5$;

Dimethyl sulfoxide, distilling by reduced pressure and preparing for use;

Potassium citrate and sodium tartrate are both analytically pure.

The experiment takes 1,2-benz-3,4-dihydrocarbazole-9-ethyl p-toluenesultonate as pre-column derivatized agent, optimizes the derivatizing and chromatographic separating conditions, carries out post column online mass spectrometry, and measures the bile acid content in the serum. The results are shown in Table 7.

TABLE 7

| | adsorption amount (mM/g) | |
| --- | --- | --- |
| | iron-based montmorillonite | cholestyramine |
| bile acid | 0 | 2.5 |
| deoxycholic acid | 0 | 4.7 |
| taurocholic acid | 0 | 4.5 |
| glycocholic acid | 0 | 4.0 |

As it is shown in Table 7, for reducing IIa type hyperlipidemia, hypercholesteremia cholestyramine medicine has absorption effect onto bile acid, while iron-based montmorillonite has totally no absorption effect onto bile acid.

EXAMPLE 6

A preparation method of the iron-based montmorillonite medicine for treating hyperphosphatemia and iron deficiency anaemia, wherein the step comprises:

(1) Weighing 500 g montmorillonite, putting them into the ultrasonic generator equipped with mixing function, then adding 5000 g deionized water that has been measured, stirring with the speed of 30 r/min, acidizing by treating with 5N hydrochloric acid until the pH value reaches to 2.4, treating by ultrasonication with 40 KHz for 30 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 3.9% by weight, powdering and screening under 400 mesh.

(2) Weighing 160 g montmorillonite prepared by step (1), putting them into the reactor equipped with mixing function, then adding 800 g deionized water that has been measured, stirring with the speed of 30 r/min, after stirring for 4 hours, loading the column by wet method (column diameter:column height=1:6), keeping the column temperature at 30, eluting by 4600 ml 5 wt % ferrous gluconate, eluting for once, twice or three time, eluting for 36 hours, then washing with deionized water until the pH value reaches to 7.0, continue washing until the excess iron ion is cleaned up, vacuum drying the iron-based montmorillonite (Fe-montmorillonite) until the water content reaches 7.3% by weight, powdering and screening under 325 mesh, obtaining lactate iron-based montmorillonite (Fe-montmorillonite). The iron ion content is 7.3% by weight in the iron-based montmorillonite (Femontmorillonite) by measurement.

(3) Preparing the iron-based montmorillonite (Fe-montmorillonite) prepared by step (2) as powder by adding and mixing evenly with powdered pharmaceutic adjuvant. The detailed method is according to the current conventional technology in the field.

EXAMPLE 7

A preparation method of the iron-based montmorillonite medicine for treating hyperphosphatemia and iron deficiency anaemia, wherein the step comprises:

(1) Weighing 500 g montmorillonite, putting them into the ultrasonic generator equipped with mixing function, then adding 5000 g deionized water that has been measured, stirring with the speed of 30 r/min, acidizing by treating with 5N hydrochloric acid until the pH value reaches to 3.2, treating by ultrasonication with 40 KHz for 30 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 2.9% by weight, powdering and screening under 400 mesh.

(2) Weighing 200 g montmorillonite prepared by step (1), putting them into the reactor equipped with mixing function, then adding 1000 g deionized water that has been measured, stirring with the speed of 30 r/min, after stirring for 40 min, adding 6000 ml 5 wt % ferrous lactate, continue stirring for 4 hours at the temperature of 30, static standing for 24 hours, separating the upper water, adding deionized water with the equal volume of the separated water for repeated washing until the pH value reaches to 6.7, continue washing until the excess iron ion is cleaned up, filtering by pressing, drying to obtain iron-based montmorillonite (Fe-montmorillonite), making the water content be 5.3% by weight, powdering and screening under 325 mesh, obtaining lactate iron-based montmorillonite (Fe-montmorillonite). The iron ion content is 6.4% by weight in the iron-based montmorillonite (Fe-montmorillonite) by measurement.

(3) Preparing the iron-based montmorillonite (Fe-montmorillonite) prepared by step (2) as particles, loading them into conventional capsule or enteric capsule to obtain medicinal capsule by adding conventional amount of pharmaceutic adjuvant and appropriate wetting agent. The detailed method is according to the current conventional technology in the field.

EXAMPLE 8

A preparation method of the iron-based montmorillonite medicine for treating hyperphosphatemia and iron deficiency anaemia, wherein the step comprises:

(1) Weighing 500 g montmorillonite, putting them into the ultrasonic generator equipped with mixing function, then adding 5000 g deionized water that has been measured, stirring with the speed of 30 r/min, acidizing by treating with 5N hydrochloric acid until the pH value reaches to 2.8, treating by ultrasonication with 40 KHz for 25 minutes, static standing and layering for 10 hours, separating the upper water, adding deionized water with the equal volume of the separated water for soaking, static standing and layering again for 10 hours, separating the upper water, repeating soaking with deionized water for several times until the pH value of the soaking buffer reaches to 6.5, filtering by pressing, drying to obtain montmorillonite, making the water content be 2.9% by weight, powdering and screening under 400 mesh.

(2) Weighing 160 g montmorillonite prepared by step (1), putting them into the reactor equipped with mixing function, then adding 800 g deionized water that has been measured, stirring with the speed of 30 r/min, after stirring for 4 hours, loading the column by wet method (column diameter:column height=1:6), keeping the column temperature at 30, eluting by 4600 ml 5 wt % ferrous lactate, eluting for once, twice or three time, eluting for 36 hours, then washing with deionized water until the pH value reaches to 6.9, continue washing until the excess iron ion is cleaned up, vacuum drying the iron-based montmorillonite (Fe-montmorillonite) until the water content reaches 6.8% by weight, powdering and screening under 325 mesh, obtaining powdered iron-based montmorillonite (Fe-montmorillonite). The iron ion content is 8.5% by weight in the iron-based montmorillonite (Fe-montmorillonite) by measurement.

(3) Preparing the iron-based montmorillonite (Fe-montmorillonite) prepared by step (2) as powder by adding and mixing evenly with powdered pharmaceutic adjuvant. The detailed method is according to the current conventional technology in the field. Alternatively, preparing the iron-based montmorillonite (Fe-montmorillonite) prepared by step (2) as particles, loading them into conventional capsule or enteric capsule to obtain medicinal capsule by adding conventional amount of pharmaceutic adjuvant and appropriate wetting agent. The detailed method is according to the current conventional technology in the field.

EXAMPLE 9

A preparation method of the iron-based montmorillonite medicine for treating hyperphosphatemia and iron deficiency anaemia, comprises the steps the same as example 1, except that the calcium-based montmorillonite (Ca-montmorillonite) is substituted by sodium-based montmorillonite (Na-montmorillonite).

EXAMPLE 10

A preparation method of the iron-based montmorillonite medicine for treating hyperphosphatemia and iron deficiency anaemia, comprises the steps the same as example 2, except that the calcium-based montmorillonite (Ca-montmorillonite) is substituted by magnesium-based montmorillonite (Mg-montmorillonite).

What is claimed is:

1. A method for preparing an iron-based montmorillonite medicine comprises:
   (1) adding pharmaceutical montmorillonite into deionized water to yield a mixture, the pH value being adjusted to 2.0-3.5 with hydrochloric acid; treating the mixture by ultrasonication under stirring for 10-30 minutes; static standing, layering the mixture and separating the upper water of the mixture; adding the deionized water into the water-removed mixture with the equal volume of the separated water for washing; separating the upper water from the mixture; repeating the washing for several times until the pH value of the washing buffer reaches 6.5-7.5; filtering the water-removed mixture by plate and frame pressing, collecting a solid material, drying the solid material until water content is no more than 10 wt %; then powdering the solid material by pulverizer until particle diameter is no more than 45 µm, then screening the solid material under 325 mesh and obtaining a medicinal montmorillonite;
   (2) soaking or eluting the medicinal montmorillonite in step (1) by a water soluble iron salt solution to yield a mixture two, washing the mixture two by the deionized water until the pH value reaches 6.5-7.5, filtering the mixture two and obtaining a solid material two, vacuum drying the solid material two, powdering the solid material two by pulverizer until the particle diameter is no more than 45 µm, then screening the solid material two under 325 mesh, obtaining the iron-based montmorillonite (Fe-montmorillonite).

2. The method according to claim 1, wherein the ultrasonic frequency in the ultrasonic treatment of the step (1) is 30-40 KHz.

3. The method according to claim 1, wherein in the step (2), soaking or eluting the medicinal montmorillonite by the water soluble iron salt solution is under the temperature of 0-40° C. for 5-72 hours, vacuum drying the solid material two until the water content is no more than 10 wt %.

4. The method according to claim 3, wherein in the step (2), soaking or eluting the medicinal montmorillonite by the water soluble iron salt solution is under the temperature of 20-30° C. for 24-48 hours, vacuum drying the solid material two until the water content is no more than 10 wt %.

5. The method according to claim 1, wherein in the step (2), the iron ion content is 5.0-9.0% by weight in the iron-based montmorillonite (Fe-montmorillonite).

* * * * *